(12) United States Patent
Jian-Feng

(10) Patent No.: US 10,495,635 B2
(45) Date of Patent: Dec. 3, 2019

(54) TESTING DEVICE FOR TESTING ANALYTES IN LIQUID SAMPLES

(71) Applicant: Abon Biopharm (Hangzhou) Co., Ltd., Hangzhou, Zhejiang (CN)

(72) Inventor: Wang Jian-Feng, Zhejiang (CN)

(73) Assignee: Abon Biopharm (Hangzhou) Co., Ltd., Hangzhou (CN)

( * ) Notice: Subject to any disclaimer, the term of this patent is extended or adjusted under 35 U.S.C. 154(b) by 0 days.

(21) Appl. No.: 15/030,852

(22) PCT Filed: Oct. 5, 2014

(86) PCT No.: PCT/CN2014/088102
§ 371 (c)(1),
(2) Date: Apr. 20, 2016

(87) PCT Pub. No.: WO2015/058612
PCT Pub. Date: Apr. 30, 2015

(65) Prior Publication Data
US 2016/0252503 A1  Sep. 1, 2016

(30) Foreign Application Priority Data

Oct. 22, 2013 (CN) .......................... 2013 1 0502781
Oct. 22, 2013 (CN) ..................... 2013 2 0657108 U

(51) Int. Cl.
*G01N 33/543* (2006.01)
*B01L 3/00* (2006.01)
*G01N 33/94* (2006.01)

(52) U.S. Cl.
CPC ...... *G01N 33/54366* (2013.01); *B01L 3/5023* (2013.01); *B01L 3/523* (2013.01);
(Continued)

(58) Field of Classification Search
CPC ............. G01N 33/54366; G01N 33/94; B01L 3/5023; B01L 3/523; B01L 2300/047;
(Continued)

(56) References Cited

U.S. PATENT DOCUMENTS 5,119,830 A  6/1992  Davis
5,595,187 A  1/1997  Davis
(Continued)

FOREIGN PATENT DOCUMENTS

CN  2 724 003 Y  9/2005
CN  1882831 A  12/2006
(Continued)

OTHER PUBLICATIONS

Extended European Search Report dated Jul. 6, 2017, regarding EP 14 856 723.3.

*Primary Examiner* — Samuel P Siefke
(74) *Attorney, Agent, or Firm* — DLA Piper LLP (US)

(57) ABSTRACT

A testing device for testing the analytes in liquid samples, including: a test chamber (115) used to accommodate testing components (102); an injection port (120); a device for gas exchange (113) between inside and out side of the testing chamber (115). The gas pressure difference makes the liquid sample enter the testing chamber (115) automatically to complete the testing of analytes in liquid samples.

4 Claims, 6 Drawing Sheets

(52) U.S. Cl.
CPC ........ *G01N 33/94* (2013.01); *B01L 2300/047* (2013.01); *B01L 2300/048* (2013.01); *B01L 2300/0825* (2013.01); *B01L 2300/0832* (2013.01); *B01L 2300/123* (2013.01); *B01L 2400/049* (2013.01); *B01L 2400/0478* (2013.01); *B01L 2400/0481* (2013.01); *B01L 2400/0688* (2013.01)

(58) Field of Classification Search
CPC ..... B01L 2300/0825; B01L 2300/0832; B01L 2300/048; B01L 2300/123; B01L 2400/0478; B01L 2400/0481; B01L 2400/049; B01L 2400/0688
See application file for complete search history.

(56) References Cited

U.S. PATENT DOCUMENTS

| | | | |
|---|---|---|---|
| 6,342,183 B1 * | 1/2002 | Lappe | ............ B01L 3/502 422/417 |
| 6,623,979 B2 | 9/2003 | Lappe et al. | |
| 6,726,879 B2 | 4/2004 | Ng et al. | |
| 7,300,626 B2 | 11/2007 | Wu et al. | |
| 2002/0009390 A1 * | 1/2002 | Lappe | ............ B01L 3/502 436/165 |
| 2002/0046614 A1 | 4/2002 | Alley | |
| 2003/0021726 A1 | 1/2003 | Wu et al. | |
| 2004/0081581 A1 | 4/2004 | Mount et al. | |
| 2005/0106750 A1 | 5/2005 | Tung et al. | |
| 2007/0092402 A1 * | 4/2007 | Wu | ............ B01L 3/502 422/400 |
| 2007/0239069 A1 | 10/2007 | Guirguis | |
| 2008/0194041 A1 | 8/2008 | Guirguis | |
| 2008/0240986 A1 | 10/2008 | Chang | |
| 2009/0308185 A1 | 12/2009 | Wu et al. | |
| 2011/0107824 A1 | 5/2011 | Lv | |
| 2011/0113901 A1 | 5/2011 | Gonzalez | |
| 2012/0270225 A1 | 10/2012 | Wakeley et al. | |

FOREIGN PATENT DOCUMENTS

| | | |
|---|---|---|
| CN | 2864667 Y | 1/2007 |
| CN | 201156047 Y | 11/2008 |
| CN | 10149855 A | 8/2009 |
| CN | 101498655 A | 8/2009 |
| CN | 101534949 A | 9/2009 |
| CN | 201464268 U | 5/2010 |
| CN | 102589928 A | 7/2012 |
| CN | 102998149 A | 3/2013 |
| CN | 203587596 U | 5/2014 |
| WO | WO 2010/003310 A1 | 1/2010 |

* cited by examiner

TESTING DEVICE FOR TESTING ANALYTES IN LIQUID SAMPLES

FIELD OF TECHNOLOGY

The present invention relates to a testing device, particularly for testing illicit drugs in liquid samples.

BACKGROUND TECHNOLOGY

Currently, it's increasingly easier for ordinary people to acquire illicit drugs, which leads to more and more use of illicit drugs. In order to guarantee the safety of working environment and fair competition of sports, enterprises, units and sports organizations need to test the body fluids of employees and athletes such as urine to see if the employees and athletes use illicit drugs. Therefore, body fluid sample collecting and testing devices are more and more widely used, with the need of being operated by non-specialists in ordinary situations. Using traditional liquid sample collecting and testing devices is inclined to cause sample leakage and the "Flooding" phenomenon due to inaccurate sample quantity or failure to test, failing to satisfy the requirements of safe testing and accurate measurement of liquid samples.

In U.S. Pat. No. 5,119,830, in a similar device in the existing technology, the testing device is placed on the lid of the urine cup. When opening the lid of the urine cup, the cup body can be used for sample collection and storage. When the test is needed, collect the sample first, and then press the protuberant part on the lid to tear the diaphragm between the testing device and the cup body, and then put the cup body upside down for a certain time to make the sample enter into the water absorbing part of the testing device along the gap which is torn so as to be tested.

In U.S. Pat. No. 5,595,187, another similar testing device is revealed, which is also set on the lid. When test is needed after collecting the sample, press a valve on the lid, make the fluid enter into a chamber temporarily, and then overturn the cup body after a certain period of time, release the valve, and the liquid sample in the chamber will contact with the testing device for testing reaction.

In addition, the public application (appl. No. US 2004/0081581) discloses a testing device, which uses filter paper to guide the liquid to the testing reagent strip. This device makes the sample solution and filter paper pad contact with each other through the overturn of cup body, and then guides the sample to further contact with the water absorbing part of the reagent strip through the filter paper. Generally, sample shortage, rather than excess samples, will occur to such device, thus leading to test failure.

In addition, the U.S. Pat. No. 6,726,879 B2 discloses a lateral-testing urine cup, which comprises three chambers: a collecting chamber, a liquid transfer chamber, and a testing chamber. Moreover, there are two lids as well, one is for sealing the collecting chamber, and the other is for testing whether the testing sample contains the analyte. This patent introduces how to realize the testing purpose by testing the liquid sample which is directly in contact with the sample receiving area in the upstream of the reagent strip.

It is still necessary to provide a new testing device, which not only can realize quantitative sampling for the liquid sample to be tested, but also is convenient for operation so as to improve the accuracy of testing.

SUMMARY OF THE INVENTION

For one aspect, the present invention provides such a testing device which comprises: a testing chamber for accommodating a test element; an injection opening; a device for gas exchanging between inside and outside of the testing chamber through the injection opening, as to make the liquid sample outside the testing chamber enter into the testing chamber through the said injection opening.

It is preferred that the space outside the said testing chamber contains a collecting chamber for collecting fluid samples. It is preferred that the said liquid sample is in the collecting chamber.

For another aspect, the present invention provides such a testing device which comprises: a testing chamber for accommodating a test element; an injection opening; a device for gas exchanging between inside and outside of the testing chamber through the injection opening, to make the liquid sample outside the collecting chamber enter into the testing chamber through the said injection opening.

For the third aspect, the present invention provides a testing device which comprises: a testing chamber for accommodating a test element; an injection opening; a liquid sample collecting chamber; a device for gas exchanging between the testing chamber and the collecting chamber through the injection opening, to make the liquid sample inside the collecting chamber enter into the testing chamber through the said injection opening.

For the last aspect, the present invention provides a testing device which comprises: a collecting chamber collecting liquid samples; a lid for sealing the opening of the collecting chamber, including a testing chamber for accommodating test elements; an injection opening; a liquid sample collecting chamber; a device for gas exchanging between the testing chamber and the collecting chamber through the injection opening to make the liquid sample inside the collecting chamber enter the testing chamber through the said injection opening.

In all the above embodiments, the gas exchanging device generates gas pressure difference inside and outside of the testing chamber, which forces the liquid sample at the injection opening enter the testing chamber.

In some preferred embodiments, the said gas exchanging device comprises a chamber for accommodating gas, the volume of which is variable, e.g., the volume decreases or increases first, or vice versa, so as to realize the gas exchanging between inside and outside of the testing chamber through the injection opening.

In some preferred embodiments, before the volume of the gas accommodating chamber changes or the gas pressure inside the testing chamber changes, the injection opening is sealed by the liquid sample outside the testing chamber. In some preferred embodiments, part of the chamber accommodating gas contains elastic flexible materials, the deformation of which will change the volume of the chamber body. In some specific embodiments, the said elastic flexible material is a kind of self-elastic deformation material, which can make the elastic components deform by external force, and discharge the gas inside the testing chamber out of the testing chamber. When the external force disappears or partially disappears, the elastic component will return to its original state, which makes the liquid in the collecting chamber enter the testing chamber through the injection opening.

It is preferred that the elastic components are deformed due to external force, which makes the gas inside the testing chamber to be discharged into the collecting chamber.

In the preferred embodiments, the gas accommodating chamber is connected to the testing chamber, or the gas pressure of the gas accommodating chamber is the same with that of the testing chamber. It is preferred that the gas accommodating chamber is connected to the testing chamber through a gas channel.

In some preferred embodiments, there are test elements for testing the analyte in the liquid sample in the testing chamber. The liquid sample entering the testing chamber through the injection opening can contact with the testing component. It is preferred that the liquid sample entering the testing chamber first contacts with the sample application area of the testing component. In some embodiments, the testing component contains water-absorbing materials, and the liquid sample can flow on the test elements due to capillary force.

In some preferred embodiments, the gas exchanging device comprises a auto-exchanging motor, which decreases the gas inside the testing chamber and hence generates negative pressure.

In some preferred embodiments, the said injection opening is near the sample receiving area of the testing component. In some other preferred embodiments, the injection opening and gas exchanging device are respectively set at both ends of the testing chamber. It is preferred that the gas exchanging device is set near the water absorbing area of the testing component.

On the other hand, the present invention provides a method of testing the analyte in the liquid sample, including: a testing chamber for accommodating test elements; an injection opening; a gas chamber for gas exchanging between inside and outside of the testing chamber through the injection opening to make the liquid sample outside the testing chamber enter the testing chamber through the said injection opening; make the liquid sample contact with the injection opening so as to seal the injection opening; make the volume of the gas chamber decrease, and let the excess gas to be discharged out of the testing chamber through the injection opening; make the volume of the gas chamber increase so that the increased volume generates negative pressure inside the testing chamber, which forces the liquid at the injection opening enter the testing chamber.

In some preferred embodiments, the volume of the said gas chamber is variable, which changes the gas pressure of the testing chamber. In some other preferred embodiments, the change of gas pressure of the testing chamber forces the liquid sample at the injection opening to enter the testing chamber. In some preferred embodiments, it is preferred that the chamber partially accommodating gas contains elastic flexible materials, the deformation of which will change the volume of the chamber accommodating gas. In some specific embodiments, the said elastic flexible material is a kind of self-elastic deformation material, which can make the elastic components deform through external force, and discharge the gas inside the testing chamber out of the testing chamber. When the external force disappears or partially disappears, the elastic component will return to its original state, which makes the liquid in the collecting chamber enter the testing chamber through the injection opening.

It is preferred that the elastic component is deformed due to external force to decrease the volume of the gas chamber, which makes the gas inside the testing chamber to be discharged into the collecting chamber.

In the above all embodiments, before generating the said gas pressure difference, the liquid sample seals the said injection opening.

Beneficial Effects

By means of the testing device of the present invention, the automatic acquisition and automatic testing of liquid samples can be realized, and meanwhile goal of quantitative sampling can be achieved.

BRIEF DESCRIPTION OF MARKS ON THE DRAWINGS

Figure 1:
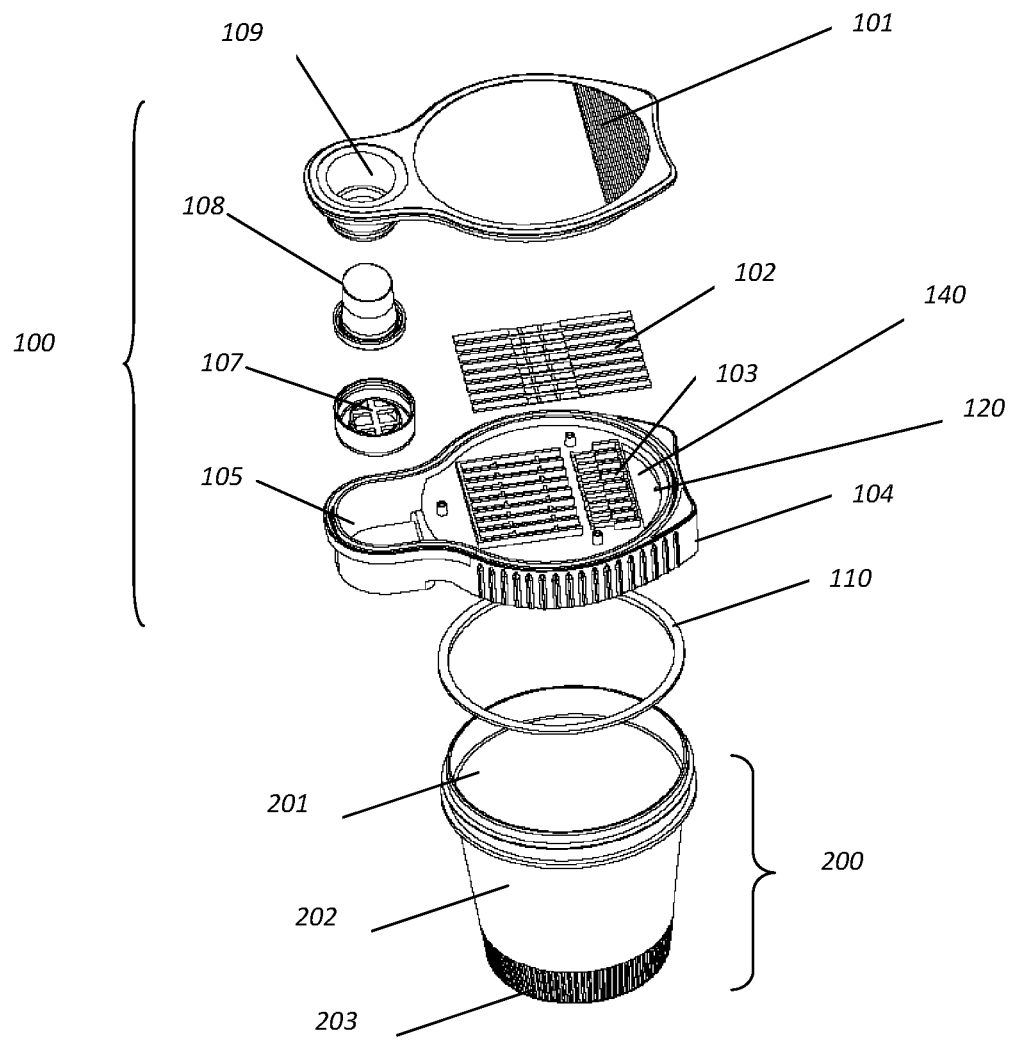
FIG. 1 shows the stereoscopic structural view of an embodiment of the present invention.
Figure 2:
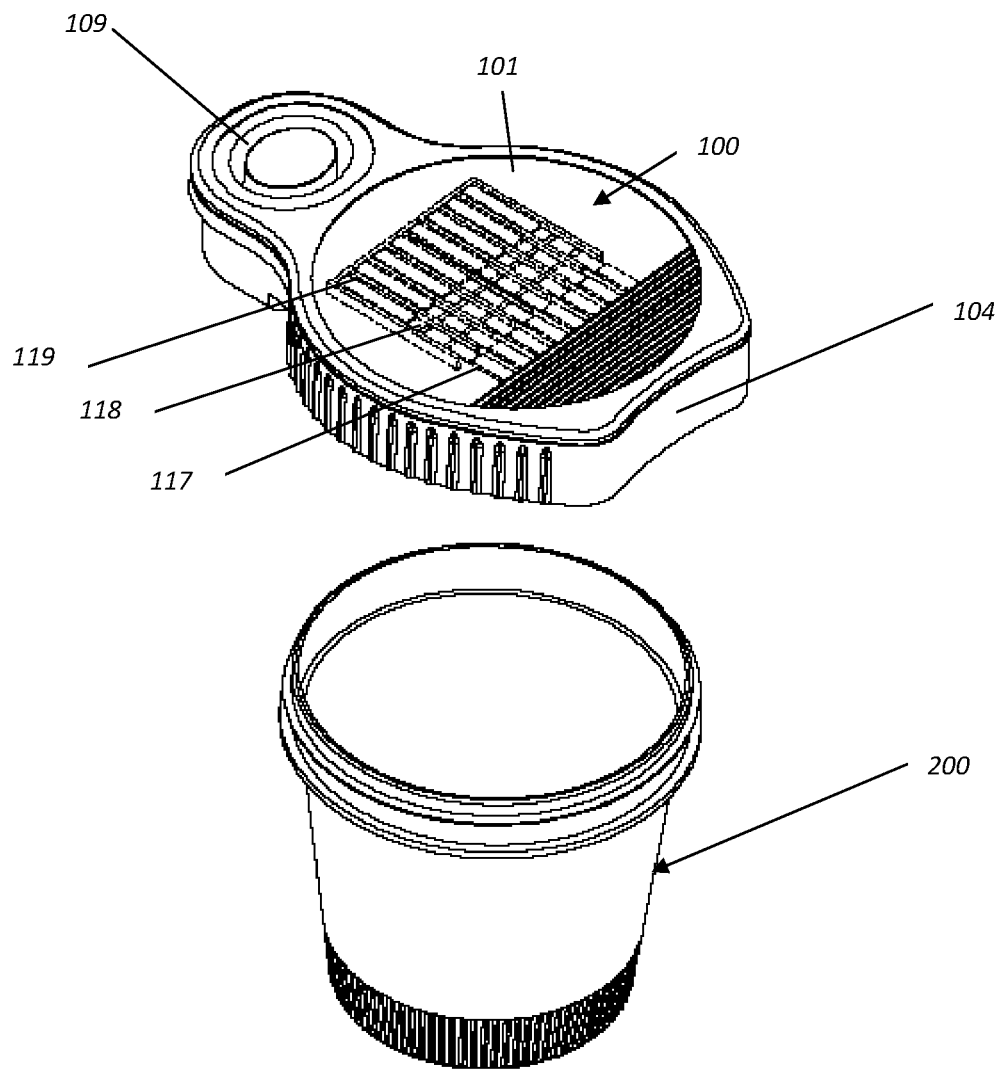
FIG. 2 shows the assembling stereoscopic structural view of another embodiment of the present invention.

Urine cup body 200; collecting chamber 202; opening 201 of the collecting chamber; bottom 203 of the collecting chamber; the protuberant 204 of the bottom of the collecting chamber; cup lid 100; upper lid 101; testing component 102; upper lid chamber 109; gas accommodating chamber 108; top 116 of the gas accommodating chamber; side wall 135 of gas accommodating chamber; gas chamber 113; fixed base 107; lower lid 104; card slot 103; injection opening 120; gas channel 114; testing chamber 115; sample receiving area 117; testing area 118; absorption area 119; lower lid chamber 105; T-slot 140; liquid sample 300; sealing ring 110; pipe 150.

DESCRIPTION OF THE PREFERRED EMBODIMENT

The structure of the present invention or the used technical terms will be further described below.

Testing

Testing is to test whether a substance or material exists, such as, but not limited to chemicals, organic compounds, inorganic compounds, metabolic products, drugs or drug metabolites, organics or organic tissue metabolites, nucleic acids, proteins, or polymers. In addition, testing also reveals the quantity of the testing substances or materials. Furthermore, testing also includes immune detection, chemical testing, enzyme testing, and etc.

Sample

The samples referred to in the present invention are those substances used to detect, test or diagnose whether the target analyte exists. Samples can be, for example, liquid samples, which may include blood, plasma, serum, urine, saliva and all kinds of fluids and can also include the liquid solution formed after pre-treating the solid samples and semisolid samples. The collected samples can be used in immunity test, chemical test, enzyme test and others to detect the existence of analyte.

Analyte

Using the devices and methods of the present invention can analyze any analyte. The analyte can be detected in any liquid or liquid sample, such as urine, saliva, saliva, blood, plasma, or serum.

The analyte can also be some hapten, including drugs (such as drug abuse). "Drug abuse" (DOA) refers to the non-medical use of drugs (usually for nerve palsy). Using this device can also detect the overdose use of drugs even for medical purpose, such as tricyclic antidepressants (imipramine or similar) and acetaminophen, etc. Those drugs will break down into different small molecules after being absorbed by human body, these small molecular substances can be found in blood, urine, saliva, sweat and other body fluids or there are small molecules partially existing in the body fluids.

Testing Device

In a specific embodiment, the testing device as provided in the present invention includes: a testing chamber for accommodating a test element, an injection opening, a gas chamber with variable volume; with the change of volume, the gas inside the testing chamber is exchanged with that of the outside liquid sample through the injection opening. In some preferred embodiments, the volume-variable gas chamber is composed of elastic flexible materials, and is connected to the testing chamber through a gas channel. When the volume of the gas chamber changes, the gas volume inside the testing chamber will also change. To balance the gas or gas pressure between inside and outside of the testing chamber, it's necessary to exchange gas through the injection opening to achieve gas pressure balance.

In addition, a test element can be placed in the testing chamber. Of course, it's not compulsory. The test element can be set in the testing chamber in advance, and can also be temporarily placed in the testing chamber before testing the analyte in the sample.

Figure 6:
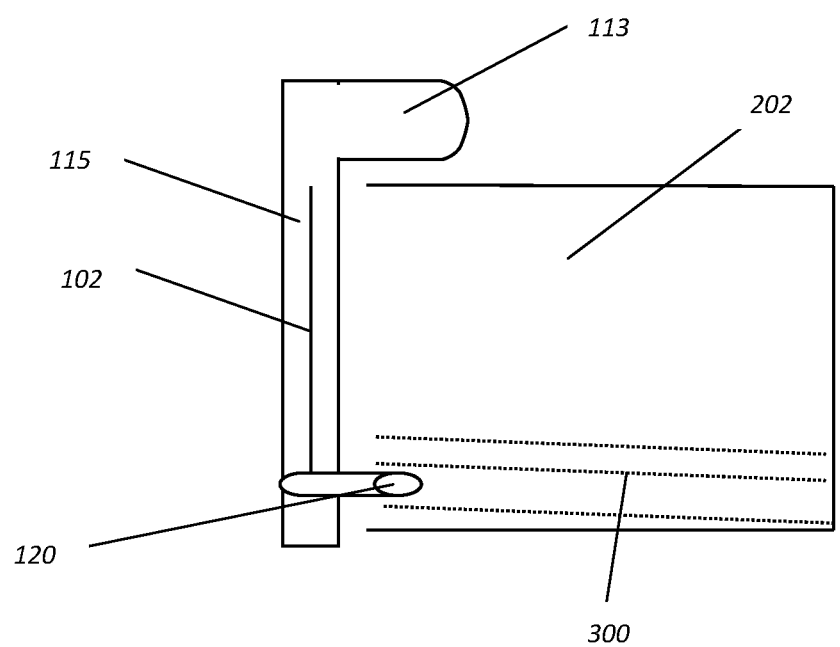
FIG. 6 shows the sectional structural view of another embodiment of the present invention.

At the time of operation, when the testing chamber contains a testing strip, keep the gas chamber in a stable state. At this point, the gas chamber is connected to the testing chamber, and the gas volume or the gas pressure inside remains unchanged. After collecting the liquid, embed the injection opening under the liquid level of the liquid sample, or let the injection opening be sealed by the liquid sample, when the testing chamber and gas chamber constitute a closed environment. At this time, let the volume of the gas chamber decrease, even to 0; the gas previously in the gas chamber will be squeezed into the testing chamber, which makes the gas in the testing chamber increase, thereby increasing pressure. The increased pressure can overcome the pressure of the liquid sealing the injection opening, and make a part of the gas be discharged out of the testing chamber through the injection opening. At that time, if the volume of the gas chamber is increased, with negative pressure generated in the testing chamber, to overcome the negative pressure, part of the liquid will enter into the testing chamber through the injection opening and contact with the testing strip to complete the testing of analyte in the sample (FIG. 6).

Of course, the following operation is also optional: when the testing chamber contains a testing strip, keep the gas chamber in a stable state. At this point, the gas chamber is connected to the testing chamber, and the volume of the gas or the gas pressure inside remains unchanged. Let the volume of the gas chamber decrease, even to 0; at this point, the gas previously in the gas chamber will be squeezed into the testing chamber, which makes the gas in the testing chamber increase, thereby increasing pressure. In this case, the internal and external pressures of the testing chamber are balanced. After collecting the liquid, embed the injection opening under the liquid level of the liquid sample, or let the injection opening be sealed by the liquid, and the testing chamber and gas chamber constitute a closed environment. At that time, if the volume of the gas chamber is increased, with negative pressure generated in the testing chamber, to overcome the negative pressure, part of the liquid will enter into the testing chamber through the injection opening and contact with the testing strip to complete the testing of analyte in the sample (FIG. 6).

In some preferred embodiments, the volume variation of the gas chamber is completed by elastic materials. For example, as part of the gas chamber is made of elastic materials, when there is external force against the elastic materials, the volume of the gas chamber is relatively smaller than that under external force, and the redundant gas is pressed into the testing chamber. On the contrary, when the external force disappears, due to the need of restoring the elasticity, the volume of the gas chamber increases, and the increased space generates negative pressure in the testing chamber, which makes the external liquid sample enter into the testing chamber through the injection opening and contact with the testing component. The specific principle and method are mentioned as above. The volume can be shrunk to 10% of the original volume, or at least 20%, or at least 35-80%, or at least 40-95%, and the volume of the gas chamber can be even reduced to 0. When the volume of the gas chamber decreases, the gas inside the testing chamber is discharged through the injection opening accordingly. When there is liquid sealing the injection opening, if the volume of the gas chamber is increased, which will generate negative pressure in the testing chamber, and the liquid sample will enter into the testing chamber through the injection opening.

In some embodiments, the volume variation of the gas chamber is completed by elastic flexible material, and the external force can be automatically added by the external devices and automatically disappear. The volume variation of the gas chamber can also be realized by piston movement. When the volume of the gas chamber changes, the gas volume or the gas pressure in the testing chamber will also change, which realizes the gas and liquid exchange through the injection opening, and hence makes the liquid sample enter into the testing chamber and contact with the test elements so as to complete the testing of the analyte in the liquid sample.

The elastic material can be selected from rubber, latex or other commonly used elastic material to achieve the goal of the present invention. In some preferred embodiments, the elastic material is latex.

Figure 3:
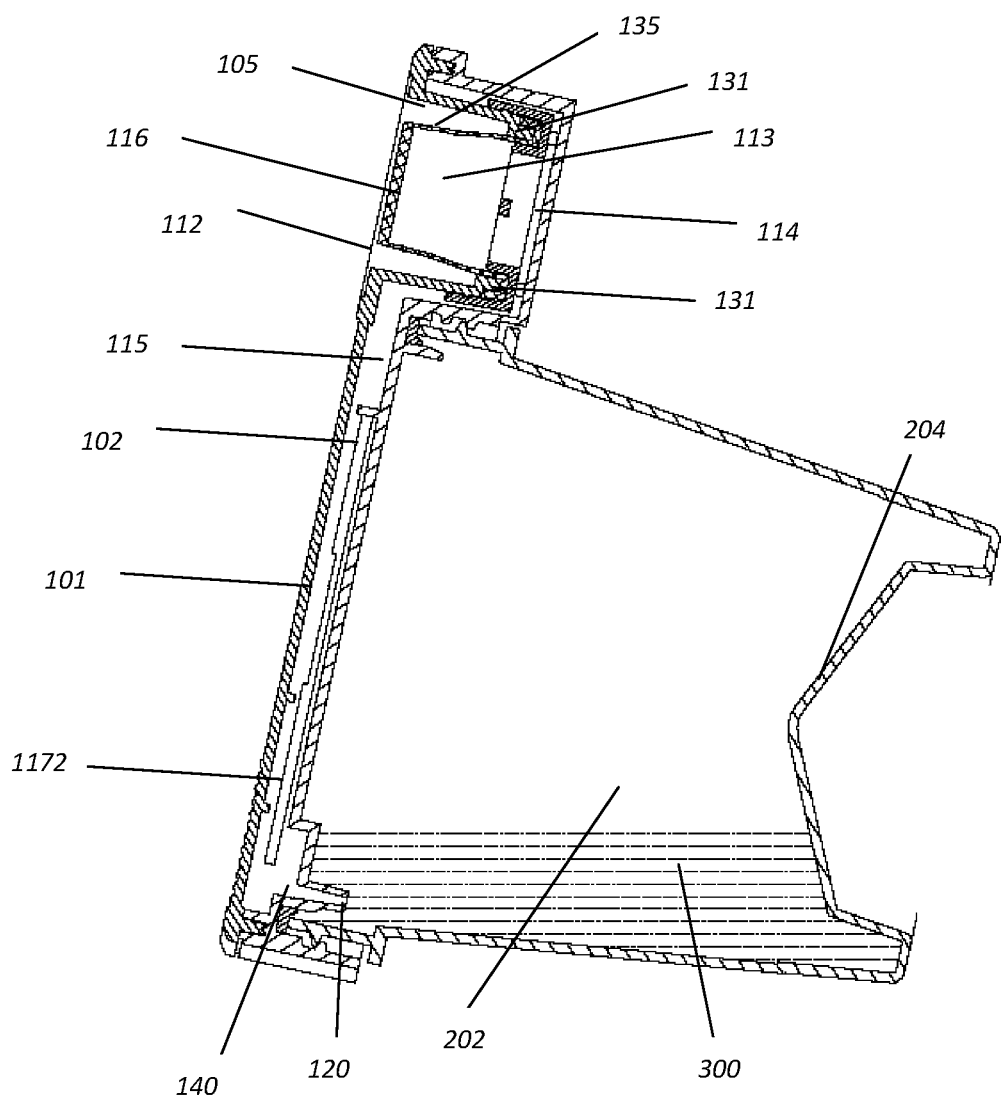
FIG. 3 shows the process schematic structure profile of an embodiment of the present invention (with the device tilted)
Figure 4:
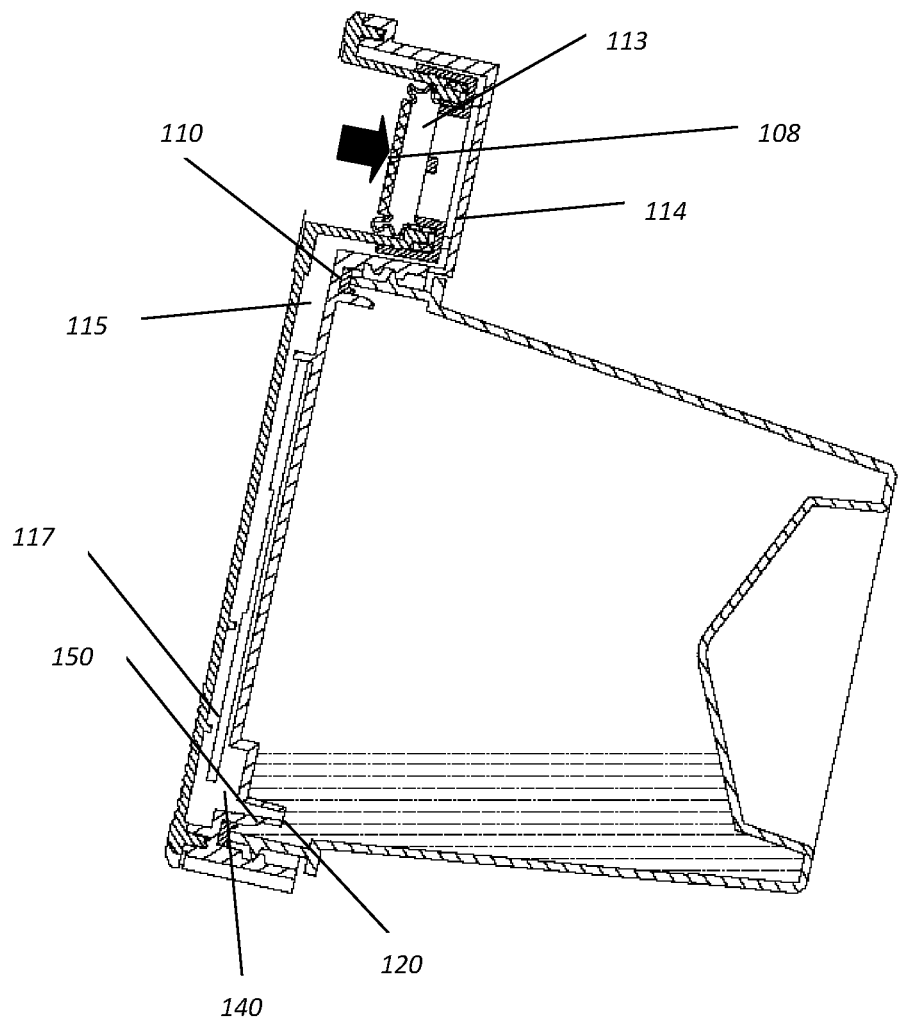
FIG. 4 shows the process diagram of an embodiment of the present invention (the volume of the gas accommodating chamber becomes smaller)
Figure 5:
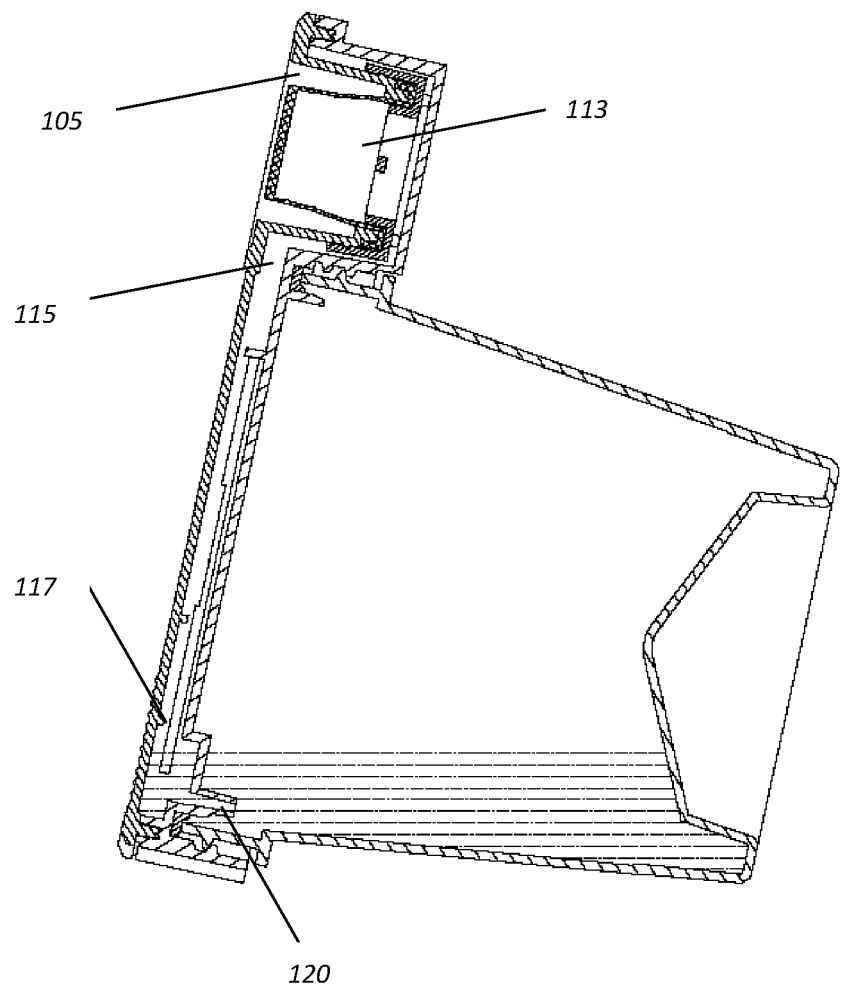
FIG. 5 shows the process diagram of an embodiment of the present invention (the volume of the gas accommodating chamber becomes bigger)

In a specific embodiment, the testing device of the present invention includes: a lid, which includes a testing chamber for accommodating a test element, an injection opening, and a gas chamber with variable volume; volume variation of the gas chamber can realize gas exchanging between inside and outside of the testing chamber through the injection opening. An example is given in FIG. 3. The lid 100 contains a testing chamber 115 for accommodating a test element, an injection opening 120, and a gas chamber 113 with variable volume, which is connected to the testing chamber, for example, through the gas channel 114. It is preferred that the testing device also contains a collecting chamber for collecting the liquid sample, and a lid for sealing the opening of the collecting chamber. At the time of operation, first use the collecting chamber to collect the liquid sample into the collecting chamber 202, for example, collect it to the collecting chamber in the cup body 200. And then use the lid body 100 to seal the opening 201 of the collecting chamber. At this point, the injection opening on the lid body does not contact with the liquid. Then, tilt the cup body 200, and let the liquid sample seal the injection opening 120. At this point, as the volume of the testing chamber and gas chamber remains unchanged essentially, there is almost no liquid entering into the testing chamber (FIG. 30). Use finger to press the gas chamber 113 to make the volume decrease, and the excess gas is pressed into the testing chamber 115, which makes the pressure of the testing chamber increase, and the excess gas is discharged to the testing chamber through the injection opening 120 (FIG. 4). Then, the external force disappears. As the gas chamber is made of elastic material, when the external force disappears, it has the ability to restore itself to the original state. At this time, the volume of the gas chamber 113 increases, which generates negative pressure in the testing chamber. To balance the pressure, the liquid sample enters into the testing chamber 115 through the injection opening 120 and contact with the testing component 102 in the testing chamber (FIG. 5). In one preferred embodiment, the diameter of the injection opening is 0.1 to 10 mm, and 0.01 to 0.5 mm, or 10-500 μm; let the injection opening have a certain surface tension, before the gas or liquid exchange between the testing chamber and collecting chamber, reduce the liquid, and even avoid the liquid from entering into the testing chamber (FIG. 3). In some other preferred embodiments, at one end of the injection opening 120 and inside the testing chamber, there is a "T" shaped notch (sectional view), and the injection opening is at one end of the pipe 150, with the other end connecting the "T" shaped notch. The accessory located at the "T" shaped notch is the sample receiving area of the testing component. In this way, liquid sample 300 entering into the testing chamber 115 through the injection opening 120 convenes at the "T" shaped notch, which enables the liquid sample with a smaller volume to fully contact with the sample receiving area.

In some preferred embodiments, the lid body comprises a upper lid body 101 and a lower lid body 104, and a testing component 102 between them, which is located in the testing chamber 115 formed between the upper and lower lids. Set a base or fixed base 107 between a concave upper lid chamber 109 formed at the upper lid and a concave lower lid chamber 105 formed at the lower lid. In addition, set the opening edge of the elastic gas accommodating chamber 108 in the base, while reserving a channel 114 for gas flow between the elastic gas accommodating chamber and the testing chamber. The channel 114 is to connect the gas accommodating chamber 108 and the testing chamber 115. The gas accommodating chamber 108 comprises a top 116 and a sidewall 135, which encircle a gas chamber 113 and made of elastic materials. The top 116 protrudes upward and is not higher than the level of the upper lid chamber 109. In this way, during use, external force can be exerted to the top 116 of the gas accommodating chamber 108, which deforms the gas accommodating chamber and changes the volume of the gas accommodating 113, such as becoming bigger or smaller. In the preferred embodiments, the volume of chamber 113 changes after the elastic material is under external force, if the external force disappears, the elastic material can return to the original state, and make the volume of the gas chamber change again. For example, when at the initial state (FIG. 3), the top is in the upper lid chamber, with the top covered by a layer of protective film 112, which is to prevent unexpected squeezing of the top of the chamber 113 which will lead to volume variation. In need of operation, unfold the protective film 112, and then squeeze the top 116 of the gas chamber 113 and make the volume of the gas chamber become smaller (FIG. 4). In this way, after the volume of the gas chamber 113 becomes smaller, the gas or air originally in the gas chamber 113 will be discharged into the testing chamber 115 through the gas channel 114. As the material of the testing chamber is substantially rigid, elastic deformation will almost not happen under such pressure. In this way, the gas pressure in the testing chamber 115 rises; to maintain the gas pressure balance inside and outside of the testing chamber, the excess gas is discharged out of the testing chamber 115 through the injection opening 120, for example, discharge into the collecting chamber 202. When the external force disappears, as the top 116 and sidewall 135 resume their original elasticity, the volume of the gas chamber increases again, which generates negative pressure in the testing chamber 115, and makes the liquid sample 300 at the injection opening 120 enter into the testing chamber 115 and contact with the testing component 102 inside. The injection opening is set at the other side of the lid body and is opposite to the gas chamber.

In some embodiments, the testing chamber in the lid body contains one or multiple card slots 103, in which a testing component 102 is set. Meanwhile, each testing component comprises a sample receiving area 117, a testing area 118 and an absorption area 119. In the preferred embodiments, the transparent location on the upper lid body 101 corresponding to the testing area makes the reaction or reaction results in the testing area be observed directly, so that test results can be achieved.

Besides the above description, the testing chamber can also be on the sidewall of the collecting chamber. In addition, the gas chamber, testing chamber and injection opening are located at the sidewall of the collecting chamber, which are integrated with the collecting chamber. Of course, in some other embodiments, the collecting chamber 202 is not a mandatory part of the present invention.

In some other embodiments, the bottom of the collecting chamber 202 is the protrusion 204, which is to convene a small quantity of liquid sample when the chamber is tilted reach the height of the injection opening. In this way, the liquid sample can seal the injection opening.

Test Elements

Test elements can be selected from cross-flow testing strips, which can detect a variety of analytes. Of course, other proper test elements can also be used in the present invention.

Various test elements can be combined to be used in the present invention. Taking the testing strip as an example, the testing strips for analyzing the analyte (such as drugs or metabolites indicating the body status) can be in various forms, such as immunoassay or chemical analysis. Testing strips can be in competitive or non-competitive analysis model. Testing strips contain a kind of water absorbing material with a sample adding area, a reagent area and a testing area. Sample is added to the sample adding area and then flows to the reagent area by capillary action. If there exists analyte in the reagent area, the sample will be combined with the reagent. Then, the sample continues flowing to the testing area. Other reagents, such as the molecular specially combined with the analyte is fixed in the testing area. These reagents react with the analyte (if present) in the sample and then are combined in this area, or combined with a certain reagent in the reagent area. The marker for displaying the testing signals exists in the reagent area or a separate marking area.

Typical non-competitive analysis model is as follows: if the sample contains the analyte, the signal is produced; if not, then the signal will not be produced. In the competitive analysis model, if the analyte does not exist in the sample, the signal is produced; if so, then the signal will not be produced.

If the testing component is the testing strip, then the material used can be water-absorbent or not. The testing strips can include a variety of materials used for transferring liquid samples. One of the testing strip material can cover on another material, for example, the filter paper can cover on the nitrocellulose membrane. An area of the testing strip can be selected from one or multiple materials, while another area can be selected from other one or multiple materials. The testing strips can be attached to a certain supporting substance or hard surface to improve the strength of the testing strips.

The analyte is detected by the signal generation system, for example, use one or multiple enzymes with specific reactions with the analyte, and then use the method of fixing the combined substance to the testing strip to fix the combined substance of one or multiple signal generation systems to the testing area of the analyte. The substance generating signals can be in the sample adding area, reagent area, testing area, or the whole testing strip. Such substance can fill up one or multiple materials of the testing strip. Add the solution containing signal matter to the surface of the testing strip or immerse one or multiple materials of the testing strip into the solution containing signal matter. Dry the testing strip containing signal matter solution.

The areas of the testing strip can be sorted as follows: sample adding area, reagent area, testing area, controlling area, area for determining whether the sample is adulterated, and the liquid sample absorbing area. The controlling area is located behind the testing area. All of the areas can be arranged in one testing strip using only one material or different materials for different areas. Each area can directly contact with the liquid sample, or different areas are sorted according to the direction of the flow of liquid sample, with the back end of one area overlapped with the front end of another area. The used material can be filter paper with good water absorbing feature, or glass fiber or nitrocellulose membrane, and etc. The testing strips can also be in other forms.

Description of Preferred Embodiments

The specific embodiments in the present invention will be further described with drawings. Such description is not to impose any restriction to the claims of the present invention, but to illustrate how to realize the present invention, which is a specific embodiment of the present invention.

FIGS. 1-5 show one of the embodiments of the present invention. As illustrated in FIG. 1, the testing device comprises a lid body with a testing chamber formed inside, a gas accommodating chamber, and an injection opening. The lid body includes the upper lid body 101 and lower lid body 104, and the testing component 102 in the testing chamber 115 between the upper and lower lid bodies. Set a base or fixed base 107 between a concave upper lid chamber 109 formed at the upper lid and a concave lower lid chamber 105 formed at the lower lid. In addition, set the opening edge of the elastic gas accommodating chamber 108 in the base, while reserving a channel 114 for gas flow between the elastic gas accommodating chamber and the testing chamber. The channel 114 is to connect the gas accommodating chamber 108 and the testing chamber 115. The gas accommodating chamber 108 comprises the top 116 and sidewall 135, which encircle the gas chamber 113 and made of elastic materials. The top 116 protrudes upward and is not higher than the level of the upper lid chamber 109. The assembled lid bodies constitute the testing device.

At the same time, a container for collecting liquid sample is provided, such as the cup body 200, which comprises the opening 201, the collecting chamber 202 and the bottom 203. The lid body can be used to enclose or seal the opening 201. On the lid body, a sealing ring 110 is set. During use, first collect liquid sample with the collecting cup, e.g. urine; then cover the lid on the opening and tilt the complete device (see FIG. 3). In this way, the liquid sample convenes in the collecting chamber of the cup and swamps the injection opening 120, or seals the injection opening. At this point, the whole testing chamber is sealed as a closed space. As the inside and outside pressures are the same, the liquid sample will hardly enter into the testing chamber 115. At this moment, unfold the protective film 112, expose the top 116 of the gas chamber with elasticity and deformation, and use your finger or external mechanic tools to squeeze the top 116, thus decreasing the volume of the gas chamber 113. Let the gas in the gas chamber 113 enter into the testing chamber 115 through the channel 114, thus increasing the gas pressure of the testing chamber, with the excess gas discharged to the collecting chamber through the injection opening 120 (FIG. 4). Then, the external force disappears, as the elastic material has the ability to return to its original state, make the volume of the gas chamber becomes bigger, and the increased volume needs more gas to enter into the gas chamber. Then, let the gas in the testing chamber 115 enter into the gas chamber, which generates negative pressure in the testing chamber. As the pressure decreases and the pressure outside the testing chamber is higher than that inside the testing chamber, the liquid sample enters into the testing chamber and contact with the test element in the testing chamber. The entering into the liquid sample balanced the pressure difference between the testing chamber and the collecting chamber. In this way, the testing of the analyte in the liquid sample is completed. The testing results can be obtained by the transparent upper lid body or reading from the testing area.

The invention claimed is:

1. A testing device for testing an analyte in a liquid sample, comprising:
   a liquid sample collecting chamber;
   a lid configured to seal the opening of the collecting chamber, the lid having a testing chamber accommodating a test element;
   an injection opening disposed in the lid in fluid connection with the collecting chamber;
   a gas chamber in fluid connection with the collecting chamber via the testing chamber and the injection opening,
   wherein the gas chamber is configured to transition from a first configuration having an initial volume to a second configuration having a reduced volume, and resiliently transition from the second configuration back to the first configuration,
   wherein the volume of the gas chamber is reduced to the reduced volume upon transition from the first configuration to the second configuration,
   wherein the volume of the gas chamber returns to the initial volume upon transition from the second configuration to the first configuration, and
   wherein the injection opening is upstream from the testing chamber and the gas chamber is downstream from the testing chamber and the device is operable to force liquid sample from the collecting chamber through the injection opening and into contact with the test element in the testing chamber via negative pressure generated within the testing chamber and the gas chamber upon resiliently transitioning the gas chamber from the second configuration to the first configuration as the volume of the gas chamber increases to the initial volume of the gas chamber.

2. The testing device according to claim 1, wherein a liquid sample present in the collecting chamber seals the injection opening before transitioning from the first configuration to the second configuration or the second configuration to the first configuration.

3. The testing device according to claim 1, wherein the gas chamber comprises elastic deformation material.

4. The testing device according to claim 1, wherein the test element is upstream from a sample receiving area, the sample receiving area being upstream from the injection opening.

* * * * *